United States Patent [19]
Foggia et al.

[11] Patent Number: 5,782,852
[45] Date of Patent: Jul. 21, 1998

[54] PLASTIC INCISION BLADE

[75] Inventors: Donald Foggia, Ocean; Anthony F. Kuklo, Jr., Bridgewater; James A. Mawhirt, Brooklyn; Gerald Feldman, Monmouth Junction, all of N.J.

[73] Assignee: International Technidyne Corporation, Edison, N.J.

[21] Appl. No.: 934,212

[22] Filed: Sep. 19, 1997

Related U.S. Application Data

[63] Continuation of Ser. No. 722,365, Sep. 27, 1996, abandoned.
[51] Int. Cl.⁶ .................................................. A61D 17/32
[52] U.S. Cl. .................................................. 606/182
[58] Field of Search ................................. 606/166, 167, 606/181–183; 128/753

[56] References Cited

U.S. PATENT DOCUMENTS

| | | | |
|---|---|---|---|
| 5,133,730 | 7/1992 | Biro et al. | 606/182 |
| 5,201,747 | 4/1993 | Mastel | 606/166 |
| 5,584,846 | 12/1996 | Mawshirt et al. | 606/182 |

*Primary Examiner*—Michael Buiz
*Assistant Examiner*—William W. Lewis
*Attorney, Agent, or Firm*—Plevy & Associates

[57] ABSTRACT

An apparatus for implementing a skin incision has an incision blade having at least three facets and at least one sharpened apex. Each of the facets narrows down to one of the apexes. A housing having an exterior surface adapted to be placed flush against the skin and an elongated slot located on the exterior of the surface housing the incision blade. A blade pivoting mechanism located in the housing guides the incision blade through the slot. The blade pivoting mechanism has a first end and second end wherein the first end is pivotally coupled to the housing and the second end supports the incision blade. An actuatable depressing mechanism, located within the housing means, engages and holds the blade pivoting mechanism in a set position, preventing the pivotal movement of the blade pivoting mechanism within the housing. When the depressing mechanism is actuated, the blade pivoting mechanism disengages and transverses the sloped surface, displacing the second end of the blade pivoting mechanism toward the elongated slot, such that the multiple facets of the incision blade emerge from the elongated slot and incise the skin.

20 Claims, 9 Drawing Sheets

PLASTIC INCISION BLADE

This is a continuation of application Ser. No. 08/722,365, filed on Sep. 27, 1996, entitled PLASTIC INCISION BLADE now abandoned.

FIELD OF THE INVENTION

The invention relates generally to an apparatus for producing a skin incision in order to cause bleeding, and more particularly to a multiple facet disposable plastic incision blade for a finger stick device capable of producing an incision.

BACKGROUND OF THE INVENTION

Blood samples are routinely drawn from patients for use in various types of blood tests. The blood is usually taken from an appropriate area, such as the patient's fingertip. A series of mechanical devices for producing skin incisions necessary to draw blood samples have been developed.

Initially, reusable mechanical devices with disposable blades were used. To its advantage, the mechanical device prevents the patient from seeing the often unsettling scene of his skin being cut. Further, the mechanical device provides good control over the incision. However, handling of the blades during disposal presented dangers, such as being cut by the exposed edge. Further, the health problems posed by used blades are apparent. More recent health considerations, including the possibility of contracting the AIDS virus from disposed blades, have increased the need for safer devices.

Disposable devices that produce standardized skin incisions were developed to overcome the problem caused by disposable blades. The "Apparatus for Implementing a Standardized Skin Incision" disclosed in U.S. Pat. No. 4,643,189, issued to Michael Mintz on Feb. 17, 1987 and assigned to W. T. Associates, includes a housing having an elongated slot. The internal hollow contains a movable pivot arm having a first pivotal end and a second end having a cam follower. There is a cam surface upon which the cam follower of the pivot arm rides. The pivotal end of the arm includes a cutting edge, which moves transversely while the arm is pivoting. The cam controls the path of the cutting edge as it enters the slot. After the unit is triggered, the edge projects through the slot in the housing along a given path to implement the incision. After traversing the path, the cutting edge is withdrawn into the housing to prevent further use and injury. Thus, this retractable-disposable device has a rapid action that produces a scalpel-like incision of standard length. The device is fabricated from molded plastic and simple metal parts, which makes manufacturing simple and economical.

The "Disposable-Retractable Finger Stick Device" disclosed in U.S. Pat. No. 5,133,730 issued to Ladislau Biro, et al. on Jul. 28, 1992 and assigned to International Technidyne Corporation, describes a stick device where the blade moves generally in an in-and-out motion and finishes in the same location. The finger stick device includes a housing having an elongated slot. The internal hollow contains a blade and a blade-pivoting mechanism for pivotally guiding the blade through the elongated slot. A first end of the blade pivoting mechanism is pivotally coupled to the housing. The second end of the blade pivoting mechanism has an upper surface and a lower surface. The blade is affixed to the second end such that its cutting edge extends away from the lower surface. The upper surface of the second end is sloped. The finger stick device further includes a depressing mechanism, which traverses the sloped upper surface of the blade pivoting mechanism, for depressing the second end of the pivoting mechanism, such that the blade moves in an arcuate motion, in which its cutting edge traverses the elongated slot and incises the skin. The incising operation is complete after the depressing means traverses the sloped upper surface.

One of the shortcomings of the metal bladed finger stick device is the blade is thin and feathers and flexes. In addition, it is difficult to obtain a sharp edge without expensive sharpening.

It is desired to provide a blade that maintains its sharpness and is not easily deformed. It is further desirable to provide a disposable-retractable finger stick device which is easily recycled.

SUMMARY OF THE INVENTION

This present invention is directed to an apparatus for implementing a skin incision. The apparatus has an incision blade having at least three facets and at least one sharpened apex. Each of the facets narrows down to one of the apexes. A housing has an exterior surface adapted to be placed flush against the skin and an elongated slot located on the exterior of the surface housing the incision blade. A blade pivoting mechanism located in the housing guides the incision blade through the slot. The blade pivoting mechanism has a first and second end wherein the first end is pivotally coupled to the housing and the second end supports the incision blade. An actuatable depressing mechanism, located within the housing means, engages and holds the blade pivoting mechanism in a set position, preventing the pivotal movement of the blade pivoting mechanism within the housing. When the depressing mechanism is actuated, the blade pivoting mechanism disengages and transverses the sloped surface, displacing the second end of the blade pivoting mechanism toward the elongated slot, such that the multiple facets of the incision blade emerge from the elongated slot and incise the skin.

One object, feature and advantage resides in the entire apparatus in a preferred embodiment, being made of a plastic which allows for ease in recycling after it use.

Further objects, features, and advantages of the present invention will become more apparent to those skilled in the art as the nature of the invention is better understood from the accompanying drawings and detailed descriptions.

BRIEF DESCRIPTION OF THE DRAWINGS

For the purpose of illustrating the invention, there is shown in the drawings forms which are presently preferred; it being understood, however, that this invention is not limited to the precise arrangements and instrumentalities shown.

DETAILED DESCRIPTION OF THE PREFERRED EMBODIMENTS

Figure 1:
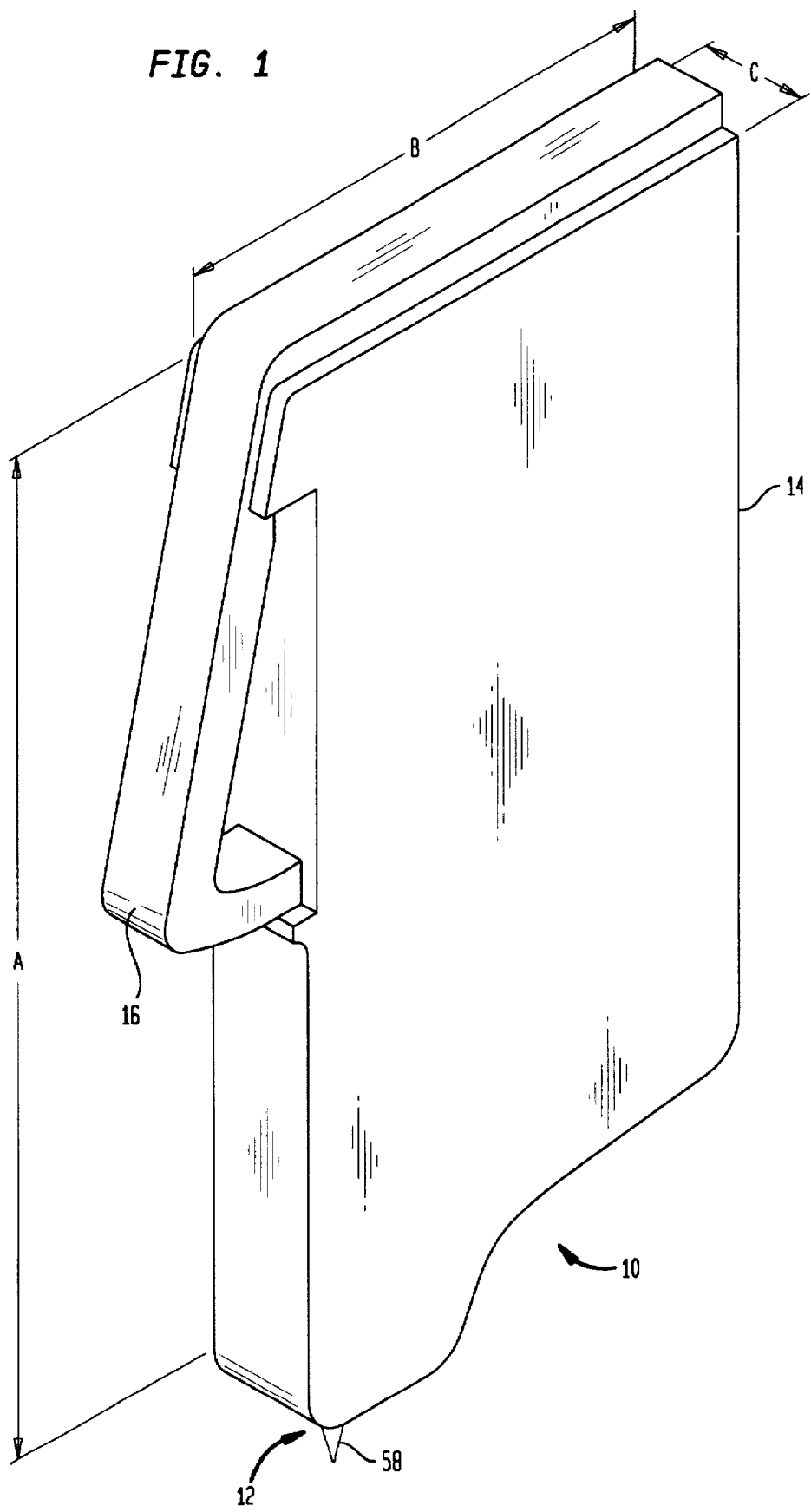
FIG. 1 is a perspective view of a finger stick device with a portion of an incision blade according to the present invention shown.

Referring now to the drawings, wherein like numerals indicate like elements and where prime ('and ") indicates counterparts of such like elements, there is shown in FIG. 1 a perspective view of a finger stick device 10 which has been identified by the numeral 10. The finger stick device 10 has an incision blade 12 in accordance with the present invention.

The visible elements of the finger stick device 10 in FIG. 1 include a housing 14, the incision blade 12, which is partially enclosed by the housing 14, and a lever arm 16, which protrudes from the housing 14. The position of the incision blade 12 and the lever arm 16 as shown in FIG. 1 would not occur at the same time in normal use as explained below.

The finger stick device 10 in a preferred embodiment is of the size that the housing 14 can be grasped by the hand of an operator. Typical dimensions for the housing 14 include an overall length A of 2 inches, a width B of 1 inch, and a thickness C of ¼ inch.

Figure 2:
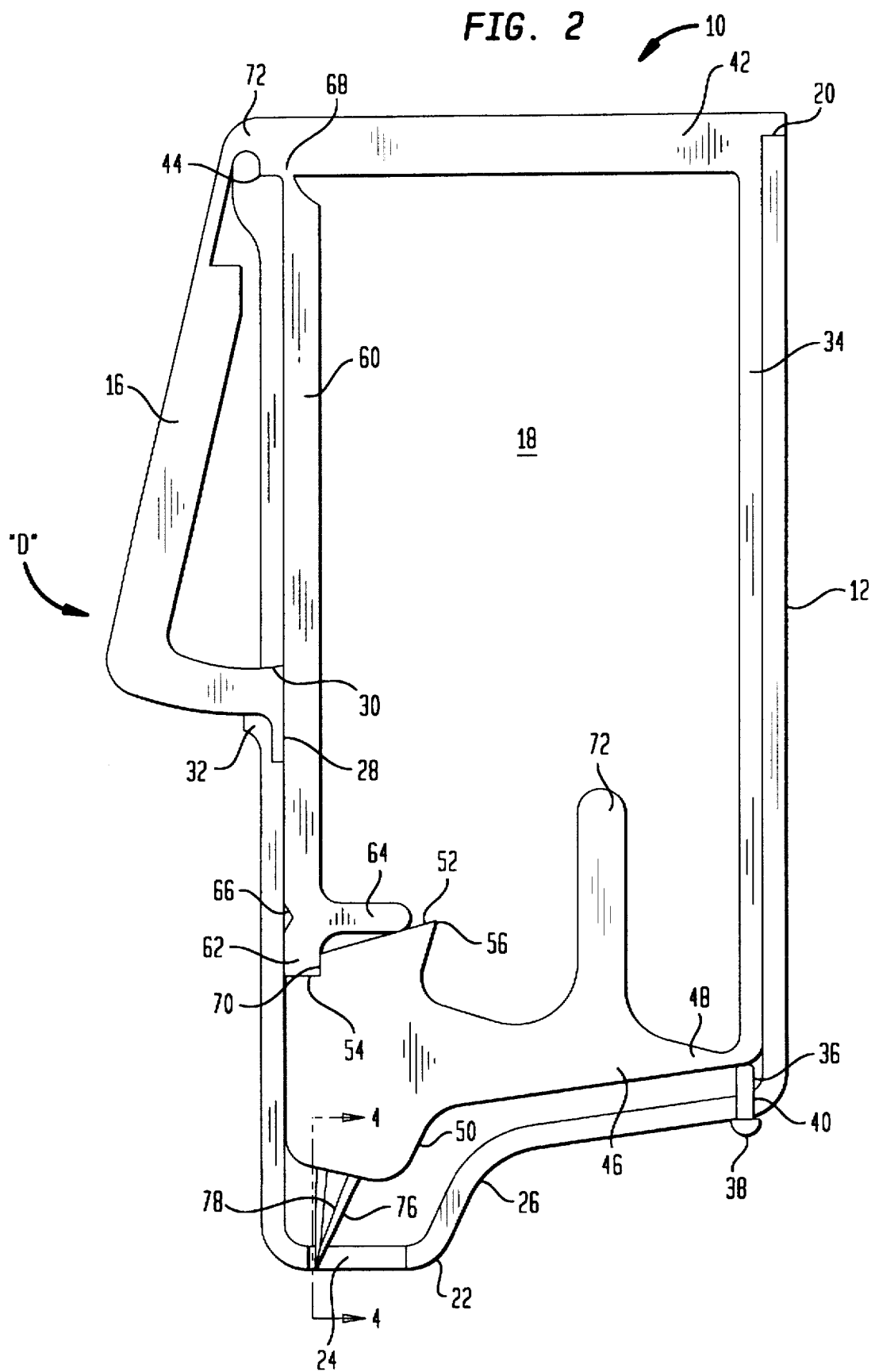
FIG. 2 is a cross-sectional view of the finger stick device illustrated in FIG. 1, taken in its quiescent state.

Referring to FIG. 2, the housing 14, which is elongated, has an internal cavity 18, an open end 20, which provides access to the internal cavity 18, and a closed end, which forms a base 22. A longitudinal slot 24 is located in the base 22. The portion 26 of the base 22 containing the longitudinal slot 24 extends away from the housing 12. This portion 26 serves to indicate to an operator the position of the longitudinal slot 24 with respect to the skin of the patient, not shown, since the exact position of the longitudinal slot 24 on the base 22 is obscured from the operator when used as explained below.

The lever arm 16, which is L-shaped, has a first end that is pivotally coupled to the housing 14 near its open end 20 and a second end which terminates in a catch 28. The catch 28 extends through a first aperture 30 located in the housing 14 and is received by a ridge 32 in the housing 14.

The finger stick device 10 has a vertical reference member 34 located across the internal cavity 18 from the aperture 30. One end of the vertical reference member 34 terminates in a projecting pin 36. A one way lock, such as a resilient projection 38, is located at the tip of the projection pin 36. The projection pin 36 and projection 38 extend through a second aperture 40 located on the base 22 of the housing 14, and function to secure the vertical reference member 34 to the housing 14. The opposite end of the reference member 34 terminates in a horizontal reference member 42, that also serves as a cover for the open end 20 of the housing. A channel 44 located at the open end 20 of the housing 14 receives one end of the horizontal reference member 42. The vertical reference member 34 and the horizontal reference member 40 comprise a support structure that is secured to the housing 14, thus, providing a mechanical coupling between components joined to the vertical reference member 34 or the horizontal reference member 42 and the housing 14.

A blade pivot arm 46 has one end that is pivotally attached to the vertical reference member 34 by a first living hinge 48. The opposite end of the blade pivot arm 46 terminates in a blade holder 50. At the upper surface of the blade holder 50 is a ramp 52, which has a positive slope. A detent 54 is located at the base of the ramp 52 and a tip 56 at the other end of the ramp 52. The incision blade 12, which has a sharpened apex 58 and will be described in more detail below, is coupled to the blade holder 50.

A bias member 60, which is elongated, has one end that terminates in two legs, one of which is a push rod 62 and the other of which is a pawl 64. A notch 66 is located above the push rod 62. The opposite end of the bias member 60 is pivotally attached to the horizontal reference member 42 by a second living hinge 68, such that the bias member 60 abuts against, but is not attached to, the catch 28 of the lever arm 16, and such that a projection 70 on the push rod 62 is received by the detent 54. When the projection 70 is received by the detent 54, the first living hinge 48 is axially prestressed, which causes the blade pivot arm 46 to lock in place. A lift lever 72, which extends towards the open end 20 of the housing 14, is located on the blade pivot arm 46, intermediate the ends of the blade pivot arm 46. The lift lever 72 functions to help retract the incision blade 12 into the housing 14, as explained below.

With the exception of the incision blade 12, the above finger stick device 10 is described in U.S. Pat. No. 5,133,730, "Disposable-Retractable Finger Stick Device," which is herein incorporated by reference. The incision blade 12 of the instant invention has at least three facets which extend from the blade holder 50 to the sharpened apex 58. In a preferred embodiment shown in FIGS. 1–6, the incision blade 12 has six facets of which only three 76 and 78 of the facets are shown in FIG. 2.

Figure 3:
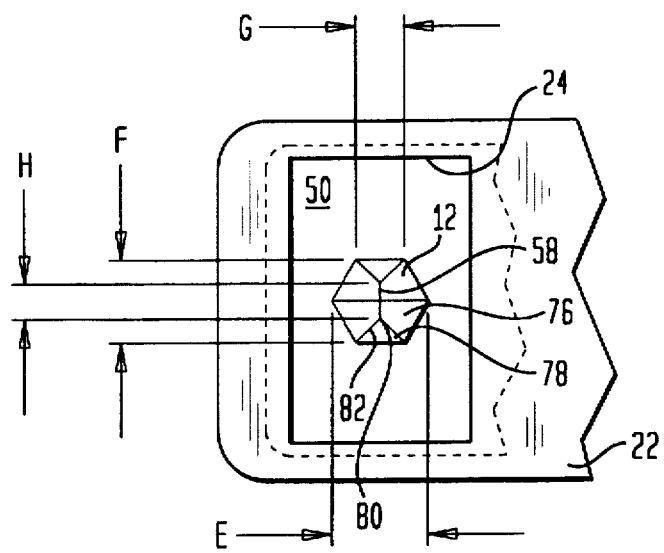
FIG. 3 is a sectional view of the incision blade projecting through a longitudinal slot in the finger stick device taken along line 3—3 in FIG. 5.

The incision blade 12 as shown in FIG. 3 projects out through the longitudinal slot 24. The incision blade 12 projects downward, out of the page in FIG. 3, from the blade holder 50, which is shown broken away in hidden line, to the sharpened apex 58. The incision blade 12 has six facets 76 and 78 of which four facets 76 are identical and extend from the blade holder 50 to the sharpened apex 58. The other two facets 78 are identical to each other and extend from the blade holder 50 only partially to the sharpened apex 58, and each stop at an intermediate apex 80.

In the preferred embodiment shown, typical dimensions of the incision blade 12 include an overall width E of 0.0616 inches and a depth F of 0.0471 inches. The width G of the base of each of the facets 78, which are located in contact with the blade holder 50, is 0.0280 inches. The facets 78 each project from the blade holder 50 to the intermediate apex 80, wherein the apexes 80 of the facets 78 are spaced apart by a distance H of 0.0191 inches.

Figure 4:
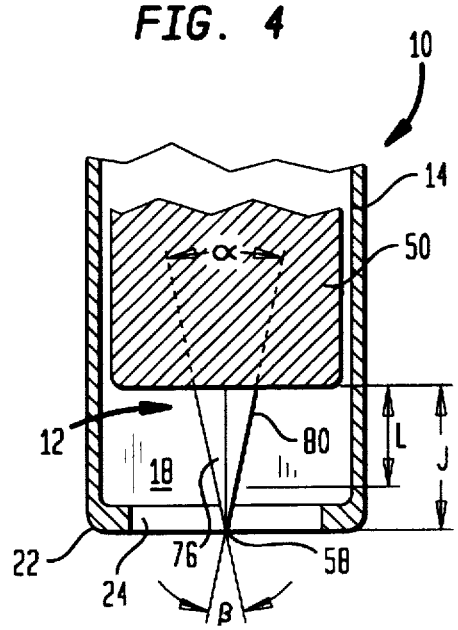
FIG. 4 is a side view of the incision blade taken along line 4—4 in FIG. 2.

Referring to FIG. 4, the incision blade 12 is shown in the internal cavity 18 of the housing 14. The apex 58 of the incision blade 12 in this position is located in the longitudinal slot 24 of the base 22. Only two of the facets 76 of the incision blade 12 are seen. The facets 76 extend from the blade holder 50 to the apex 58 which is a distance J of 0.1150 inches in the preferred embodiment. The edge of the facets 76 changes angle at the location of the intermediate apex 80 of the facets 78, which are not seen. The intermediate apex 80 of the facets 78 is a distance L of 0.0794 inches from the blade holder 50.

Figure 5:
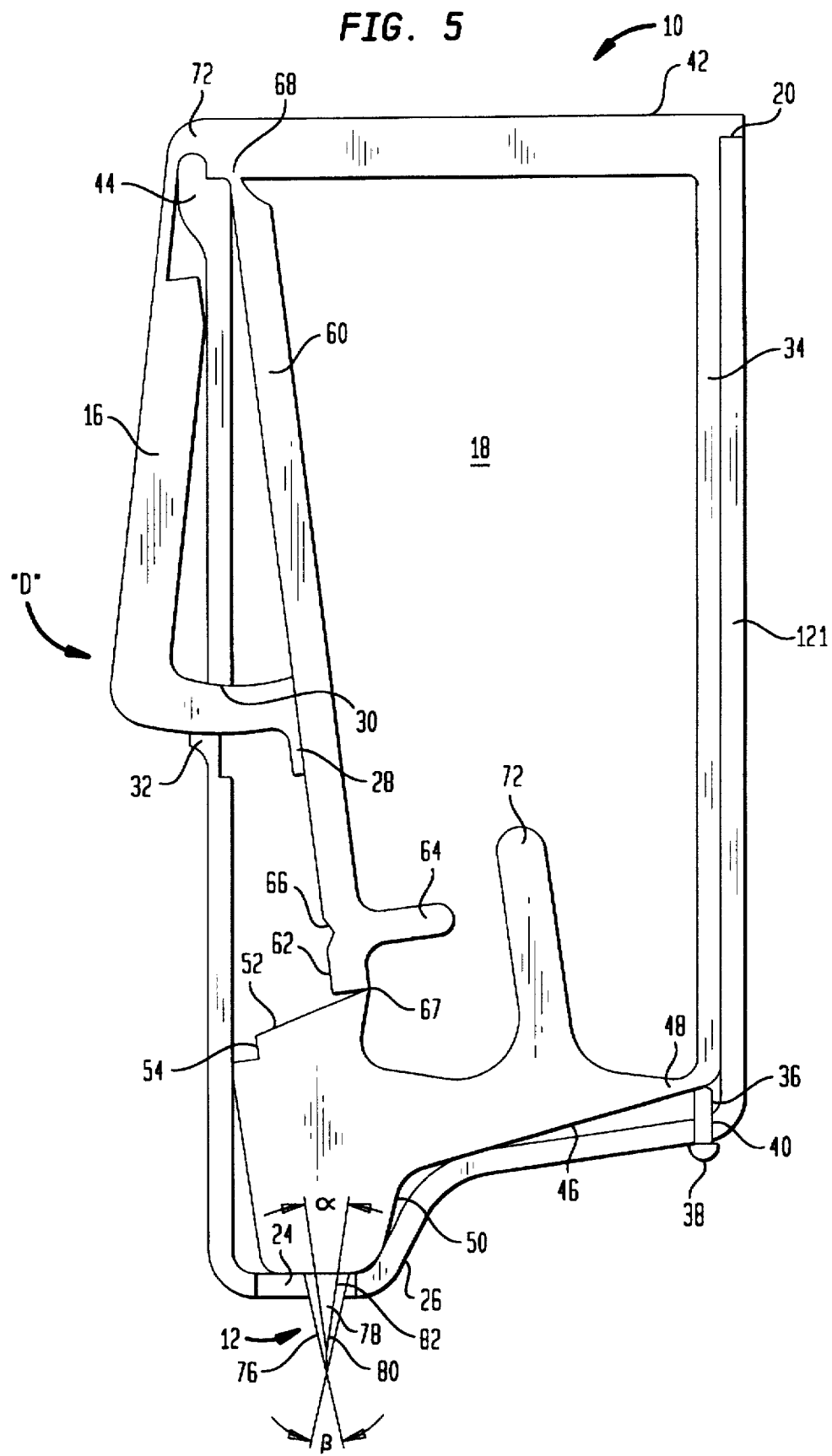
FIG. 5 is a cross-sectional view of the finger stick device illustrated in FIG. 1, taken while the blade is making an incision.

Referring to FIG. 5, each of the two facets 78, only one seen, have a pair of sides 82 which project up from the blade holder 50 to the formation of an angle βof 20 degrees in a preferred embodiment. The two opposing edges between the two adjoining facets 76 form an angle βof 30 degrees.

While the finger stick device 10 as disclosed does not have to be formed integrally, the vertical reference member 34, the horizontal reference member 42, the bias member 60, the lever arm 16, the blade pivot arm 46 including the blade holder 50, and the incision blade 12 can be formed integrally to ease manufacturing and fabrication. The finger stick mechanism including the bias member needs to be a resilient material and the incision blade 12 needs to be a non-brittle material which holds the edge of the facets (i.e., maintains its sharpness) and does not flash beyond the desired edge, point, wedge or chisel. In a preferred embodiment, the material that can satisfy the varied requirements could be a polycarbonate such as Bayer Makralon 2458 or an acetal, an acetal copolymer or a polyester as supplied by Dupon, GE or Dow.

In that the entire finger stick device 10 is manufactured from only a plastic, after the single use, the finger stick device 10 can be disposed to a facility where the finger stick device 10 can be melted down to allow for recycling or reclaiming of the plastic.

In Operation

Referring to FIG. 2, the operator holds the finger stick device 10 with one hand such that the housing is firmly grasped and places the bottom surface flush against the patient's skin, not shown, at the location where the incision is desired, and squeezes the lever arm 16. The depression of the lever arm 16 irreversibly actuates the finger stick mechanism located in the housing 14. The finger stick mechanism causes the incision blade 12 to exit the housing and to puncture the patient's skin, and immediately thereafter, to retract back into the housing 14. Once depressed, the lever arm 16 cannot reactuate the finger stick mechanism; therefore, the incision blade 12, once used, is located permanently within the housing 14.

When the lever arm 16 is depressed in the direction of the arrow "D", its catch 28 pushes against the bias member 60. Because the projection 70 is engaged with the detent 54, the bias member 60 flexes which causes it to store energy. This stored energy, when released, is channeled to depress the blade holder 50. As the bias member 60 is flexed, its effective length decreases to cause the blade support arm 46 to pivot upward. The flexure of the bias member 60 also causes the pawl 64 to engage the top surface of the ramp 52. The pawl 64 depresses the ramp 52 to cause the projection 70 to disengage from the detent 54. Once disengaged, the flexed bias member 60 simultaneously unflexes and pivots about the living hinge 68, causing the push rod 62 to rapidly traverse the ramp 52. As a result of these actions, the push rod 62 irreversibly traverses the ramp 52, thereby depressing the blade holder 50 and causing it to pivot about the vertical reference member 34 (see FIG. 5). As the incision blade 12 is pivoted, its apex 58 and multiple facets 76 and 78 move traversely through the longitudinal slot 24 and incises the patient's skin, until the blade pivot arm 46 abuts against the extended portion 26 of the housing 14. The incision blade 12 makes an incision at a relatively predetermined depth sufficient to incise blood vessels, such that a blood sample can be drawn from the patient.

Unlike thin disposable blades, the incision blade 14 does not feather or flex because of its three dimensional shape. In addition, the incision blade 14 as formed in an injection mold has sufficiently sharp edges to eliminate the need for additional sharpening before use.

Referring to FIG. 5, after the push rod 62 traverses the ramp 52, the pawl 64 strikes the lift lever 72, whereupon the blade pivot arm 46 reverses direction and pivots the incision blade 12 into the housing 14. This retraction of the incision blade 12 is aided by the plastic memory of the first living hinge 48. Thus, immediately after the incision is implemented, the blade is caused to retract into the housing 12.

Figure 6:
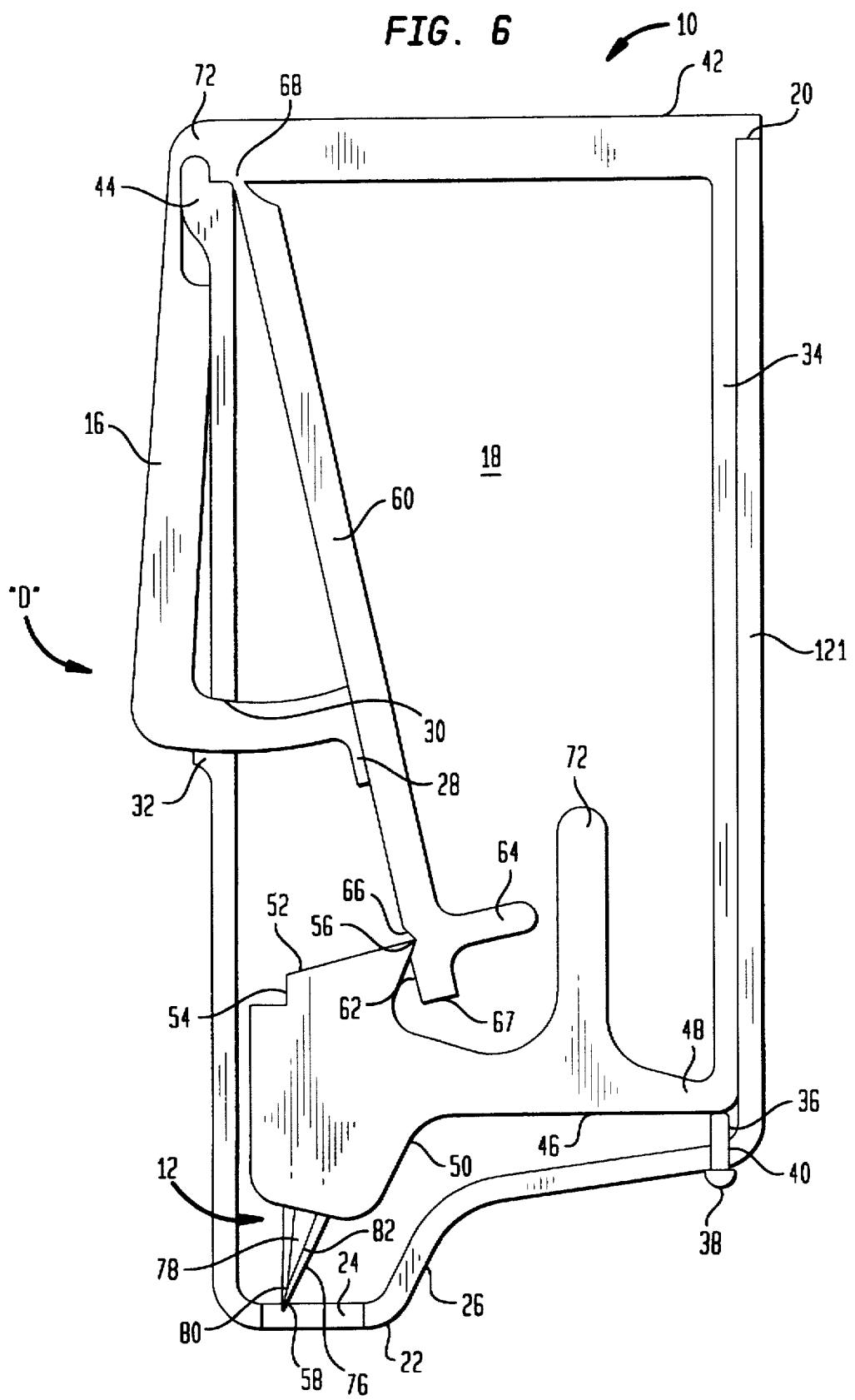
FIG. 6 is a cross-sectional view of the finger stick device illustrated in FIG. 1, taken after the finger stick mechanism was actuated.

Referring to FIG. 6, at the point where the pawl 62 and the lift lever 72 collide, the bias member 60 has expended most of its stored energy. Due to this loss of energy, and due to the plastic memory of the second living hinge 68, the bias member 60 begins to pivot back to the quiescent position, whereupon the notch 66 engages the tip 56 of the ramp 52, thereby locking the blade pivot arm 46 in a final, stationary position as seen in FIG. 6. The plastic memory of the second living hinge 68 urges the bias member 60 against the tip 56 of the ramp 52 on the blade holder 50. Thereafter, the lever arm 16 cannot extend into the housing 14 far enough to disengage the bias member 60 from the ramp 52, and the incision blade 12 is permanently locked within the housing 14.

Alternative Embodiment

Figure 7:
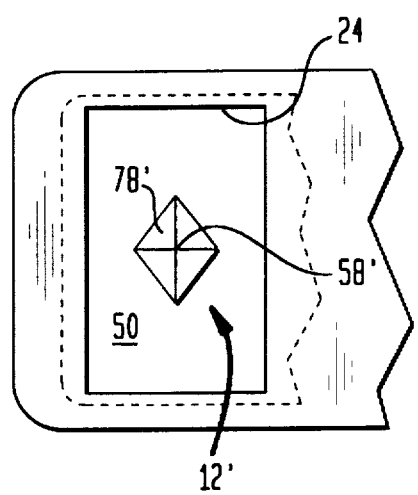
FIG. 7 is a bottom view similar to FIG. 3 of an alternative embodiment of the incision blade.
Figure 7A:
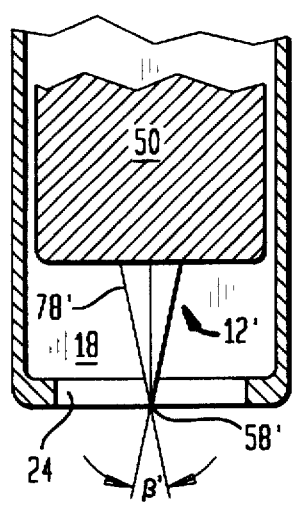
FIG. 7A is a side view similar to FIG. 4 of the alternative embodiment of the incision blade.

FIGS. 7 and 7A show an alternative incision blade 12', which projects out through the longitudinal slot 24. The incision blade 12' projects downward, out of the page in FIG. 7, from the blade holder 50, which is shown broken away in hidden line, to a sharpened apex 58'. The two opposing edges between adjoining facets 78' form an angle β' of 30 degrees. There are no additional facets which extend from the blade holder 50 only partially to the sharpened apex as in the first embodiment.

Figure 8:
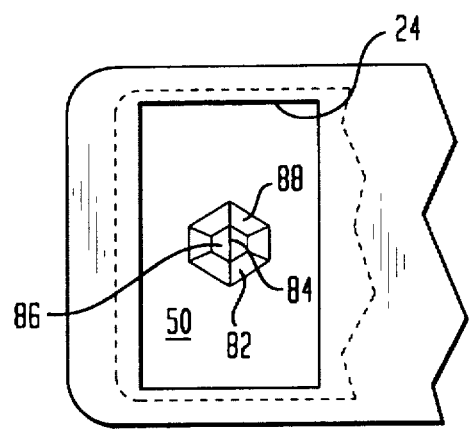
FIG. 8 is a bottom view similar to FIG. 3 of another alternative embodiment of the incision blade.
Figure 8A:
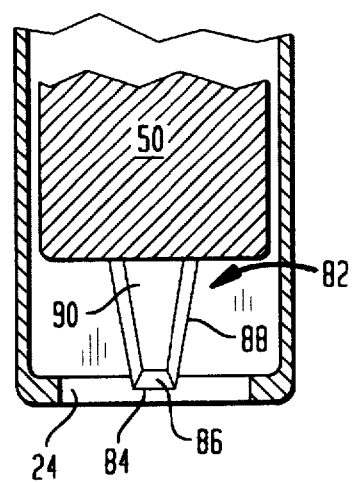
FIG. 8A is a side view similar to FIG. 4 of the alternative embodiment of the incision blade shown in FIG. 8.

FIGS. 8 and 8A show another alternative incision blade 82, which projects out through the longitudinal slot 24 in FIG. 8A. The incision blade 82 projects downward, out of the page in FIG. 8, from the blade holder 50, which is shown broken away in hidden line, to a wedge-like sharpened apex 84. The incision blade 82 has a pair of trapezoid shaped facets 86 forming a wedge, and an additional four facets 88 extending from the apex 84. The four facets 88 are triangular-shaped and are located in two sets with the two in one set having a common edge. In addition, the incision blade 82 has two additional facets 90. Each facet 90 extends from the larger base of one of the facets 86 to the blade holder 50.

Figure 9:
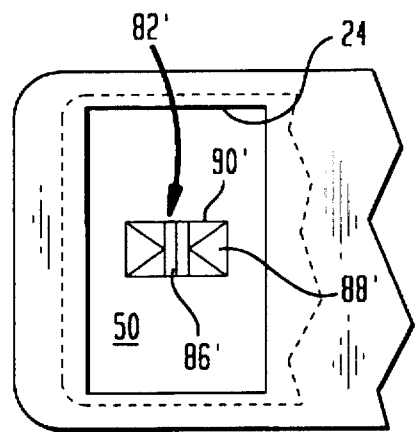
FIG. 9 is a bottom view similar to FIG. 3 of another alternative embodiment of the incision blade.
Figure 9A:
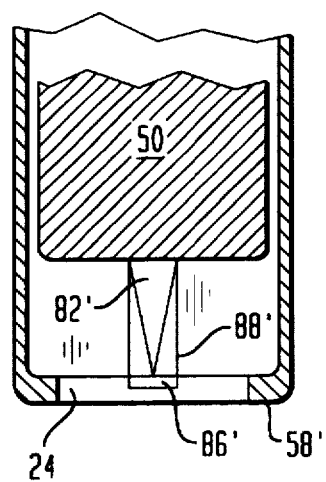
FIG. 9A is a side view similar to FIG. 4 of the alternative embodiment of the incision blade shown in FIG. 9.

FIGS. 9 and 9A show another alternative incision blade 82', which projects out through the longitudinal slot 24. The incision blade 82' projects downward, out of the page in FIG. 9, from the blade holder 50, which is shown broken away in hidden line, to a chisel-like sharpened apex 84'. The incision blade 82' has a pair of rectangular shaped facets 86 forming a chisel. Six additional facets 88' extend from the edge of the facets 86', three from each facet 86' to the blade holder 50. In addition, the incision blade 82' has two additional edge facets 90' hidden from view.

Figure 10:
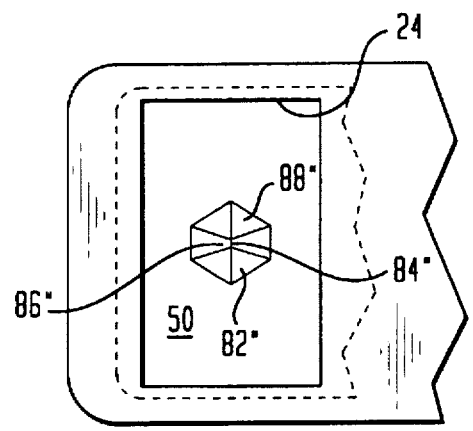
FIG. 10 is a bottom view similar to FIG. 3 of another alternative embodiment of the incision blade.
Figure 10A:
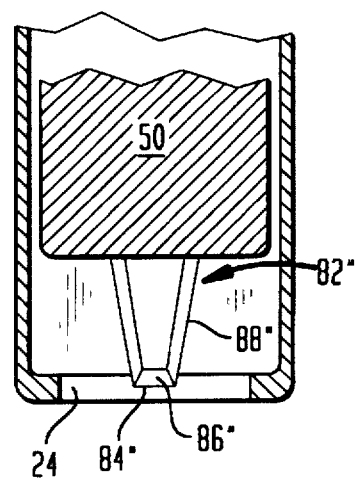
FIG. 10A is a side view similar to FIG. 4 of the alternative embodiment of the incision blade shown in FIG. 9.

FIGS. 10 and 10A show another alternative incision blade 82", which projects out through the longitudinal slot 24. The incision blade 82" projects downward, out of the page in FIG. 10, from the blade holder 50, which is shown broken away in hidden line, to a wedge-like sharpened apex 84". The incision blade 82" has a pair of trapezoid shaped facets 86" forming a wedge, and an additional four facets 88" extending from the apex 84". The four facets 88" are triangular-shaped and are located in two sets with the two in one set having a commion edge. The trapezoid shaped facets extend to the blade holder 50.

The present invention may be embodied in other specific forms without departing from the spirit or essential attributes therefore and, accordingly, references should be made to appended claims, rather than to the foregoing specification, as indicating the scope of the invention.

It is recognized that other style finger stick devices can include the multi-faceted incision blade. For example, the housing of the device can be formed out of two halves as disclosed in U.S. Pat. No. 5,133,730, in contrast to an open container and use the horizontal reference member as a cover.

We claim:

1. A blade for making a skin incision, the blade comprising:

a three-dimensional plastic member having a pyramidal outer peripheral surface defined by at least four individual facets, each facet being oriented in a different plane, and wherein at least two of the facets converge at a terminus to define an incision-making area, wherein the incision making area is oriented in a plane intersecting and relatively transverse to the planes of the at least two converging facets.

2. The blade according to claim 1, wherein the incision-making area comprises one sharpened apex point, and wherein all the facets narrow down to and meet at the one apex point.

3. The blade according to claim 2, wherein the facets are generally triangular in shape, and the vertices of the triangular facets converge at the apex.

4. The blade according to claim 1, wherein the terminus is formed by adjoining lateral edges of at least two of the facets such that the incision-making area comprises an edge running substantially parallel to the base of the blade.

5. The blade according to claim 4, wherein the terminus of the blade has a width of about 0.01 to 0.02 inches.

6. The blade according to claim 1, wherein the at least two facets that converge to define the incision-making area of the blade have opposing planes that are disposed at an angle of approximately 30 to 45 degrees relative to each other.

7. The blade according to claim 1, wherein the plastic member has two sets of facets, wherein each set of facets contains at least two facets; wherein one set of facets comprises cutting facets that join at the terminus to define the incision-making area, and wherein the second set of facets comprises supporting facets, wherein each one of the supporting facets terminates at an edge of a cutting facet thereby serving to buttress the cutting facets.

8. The blade according to claim 7, wherein two of the cutting facets are substantially the same size and shape relative to each other, and two of the supporting facets are substantially the same size and shape relative to each other.

9. The blade according to claim 7, wherein the cutting facets comprise two trapezoidal-shaped facets that join to form a wedge-shaped point at the terminus.

10. The blade according to claim 7, wherein the cutting facets comprise two rectangular-shaped facets that join to form a chisel-shaped point at the terminus.

11. The blade according to claim 7, wherein the plastic member further comprises four cutting facets that are generally triangular in shape and disposed in two pairs of two facets such that the facets in each pair share a common edge and have two opposing side edges, and wherein all four cutting facets narrow to a common sharpened apex point for making an incision; and two supporting facets, wherein one supporting facet is sandwiched between both pairs of cutting facets, such that each supporting facet bridges an opposing side edge of one pair of cutting facets to an opposing side edge of the other pair of cutting facets and thereby completes the circumference of the outer peripheral surface of the blade.

12. The blade according to claim 11, wherein the two supporting facets are generally triangular in shape, and wherein each one of the supporting facets extends from the base of the blade and terminates at a point located along an opposing side edge of a cutting facet, such that the terminus of one supporting facet defines an intermediate apex point disposed along one side edge of the blade and the terminus of the other supporting facet defines an intermediate apex point disposed along the other side edge of the blade.

13. The blade according to claim 12, wherein the width of the blade at the base of the facets is about 0.02 to 0.065 inches; wherein the length of the blade from the base to the apex is about 0.10 to 0.12 inches; and wherein the intermediate apex points are spaced apart on either side of the blade by about 0.01 to 0.02 inches.

14. The blade according to claim 7, wherein the plastic member further comprises two cutting facets each having an upper edge and a lower edge; wherein the upper edges of the cutting facets converge at the apex such that the incision-making area of the blade comprises an edge running substantially parallel to the base of the blade;

at least four supporting facets comprising a front facet, a back facet, and two side facets, wherein the front facet extends from the lower edge of one cutting facet to the base of the blade, and the back facet extends from the lower edge of the other cutting facet to the base of the blade; and wherein each side facet joins a side edge of the front facet to a side edge of the back facet such that the two side facets complete the circumference of the outer peripheral surface of the blade.

15. The blade according to claim 14, wherein the cutting facets are trapezoidal in shape and join to form a wedge-shaped terminus defining the incision-making area; and wherein each side facet comprises a pair of generally triangular-shaped facets sharing a common edge; and wherein each side facet extends from the base of the blade to the wedge-shaped terminus.

16. The blade according to claim 14, wherein the cutting facets are rectangular-shaped and join together at their upper edges to form a chisel-shaped terminus defining the incision-making area; and wherein the front and back supporting facets each comprise a plurality of triangular-shaped facets.

17. The blade according to claim 7, wherein the plastic member further comprises:

a front and a back cutting facet, wherein both cutting facets are trapezoidal in shape and extend from the base of the blade to the terminus to form a chisel-shaped edge at the incision-making area, the chisel-shaped terminus having a first and second corner; and two pairs of triangular-shaped side supporting facets, wherein each pair of side facets share a common side edge; wherein one pair of side facets extends from the base of the blade to the first corner of the chisel-shaped terminus, and the other pair of side facets extends from the base of the blade to the second corner of the chisel-shaped terminus; and wherein each pair of side facets is disposed between the front and the back cutting facets thereby completing the circumference of the outer peripheral surface of the blade.

18. A blade for making a skin incision, the blade comprising:

a plastic member having a pyramidal shaped outer peripheral surface defined by six individual facets, each facet being oriented in a different plane;

wherein at least two of the facets comprise cutting facets that are substantially the same size and shape and converge at a terminus to define an incision-making area, wherein the incision-making area is oriented in a plane intersecting and relatively transverse to the planes of the cutting facets; and wherein at least two of the facets comprise supporting facets that are triangular in shape, are substantially the same size and shape, and terminate at an edge of a cutting facet thereby serving to buttress the cutting facets.

19. An improved finger-stick device for making a skin incision of the type having a housing means with a slot adapted to be placed flush against the skin, a blade support arm for holding a blade within the housing means, and a biasing means for resiliently guiding the blade through the slot in the housing means to prick a person's finger, wherein the improvement comprises a plastic blade disposed on the blade support arm, the plastic blade comprising:

a plastic member having a pyramidal shaped outer peripheral surface defined by at least four individual facets, each facet being oriented in a different plane, and wherein at least two of the facets converge at a terminus to define an incision-making area, wherein the incision making area is oriented in a plane intersecting and relatively transverse to the planes of the at least two converging facets.

20. The improved finger-stick device of claim 19, wherein the plastic member further comprises two sets of facets, wherein each set of facets contains at least two facets; wherein one set of facets comprises cutting facets that join at the terminus to define the incision-making area, and wherein the second set of facets comprises supporting facets, wherein each one of the supporting facets terminates at an edge of a cutting facet thereby serving to buttress the cutting facets.

* * * * *